United States Patent

McKinley et al.

[11] 4,011,268
[45] Mar. 8, 1977

[54] METHOD OF PREPARING MONOETHERS OF ALKYLENE GLYCOLS

[75] Inventors: Suzanne V. McKinley, Wellesley, Mass.; Joseph W. Rakshys, Jr., Midland, Mich.

[73] Assignee: The Dow Chemical Company, Midland, Mich.

[22] Filed: Sept. 25, 1975

[21] Appl. No.: 616,727

Related U.S. Application Data

[63] Continuation of Ser. No. 390,453, Aug. 22, 1973, abandoned.

[52] U.S. Cl. .................. 260/613 D; 260/611 R; 260/611 B; 260/613 B; 260/615 R; 260/615 B
[51] Int. Cl.² .................................. C07C 41/02
[58] Field of Search ....... 260/613 D, 613 B, 611 R, 260/611 B, 615 R, 615 B

[56] References Cited

UNITED STATES PATENTS

| 3,880,779 | 4/1975 | Unoura et al. ............. 260/615 B X |
| 3,910,878 | 10/1975 | McAda .................... 260/615 B X |

*Primary Examiner*—Bernard Helfin
*Attorney, Agent, or Firm*—Glwynn R. Baker

[57] ABSTRACT

The reaction of an organic monohydroxy compound with a monomeric epoxide is catalyzed by insoluble, polymeric composition having tetraalkyl phosphonium alkoxide, aryloxide or hydroxide containing pendant groups. These groups have the structure

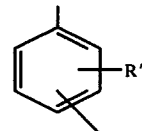
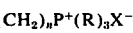
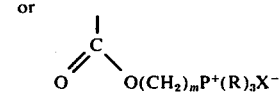

wherein $n$ is an integer from 1 to 3, preferably 3, $m$ is an integer from 1–6, preferably 3–6, R is an alkyl group of from 1 to 6 C atoms, R' is H, an alkyl, CN, or other group inert to reaction with phosphonium halides, alkoxides or the phosphonium salt resins or in some instances to organolithium reagents and X is an alkoxy, cycloalkoxy or aryloxy group, or an OH group.

The above catalysts are readily removed from the reaction mixture because of their insolubility. They are particularly useful for making monoethers of the structure $A(OA')_bOH$ where A is the nonhydroxyl residue of the monohydroxy compound and A' is the nonhydroxy residue of an epoxide monomer, and $b$ is an integer of from 1 to about 20 with $b = 1$–5 preferred.

14 Claims, No Drawings

METHOD OF PREPARING MONOETHERS OF ALKYLENE GLYCOLS

CROSS REFERENCE TO RELATED APPLICATION

This is a continuation of application Ser. No. 390,453 filed Aug. 22, 1973, now abandoned.

BACKGROUND OF THE INVENTION

It is known that certain alkali metal hydroxides, amines, tertiary phosphines and quaternary ammonium hydroxide resins will catalyze the reaction between a monohydroxy compound and a vicinal epoxide to produce either a monomeric ether of the corresponding monoglycol or a monoether of a polyalkylene glycol. When soluble catalyst such as certain alkali metal hydroxides, low molecular weight amines or tertiary phosphines are used, the catalyst is removed from the reaction mixture with difficulty. When a polymeric, insoluble, quaternary ammonium hydroxide is the catalyst, it deteriorates readily at the reaction temperatures used and, thus, must either be replenished during the reaction, or the reaction may have to be terminated before completion. The quaternary ammonium hydroxide containing polymers cannot be reused for catalytic purposes.

It is, therefore, an object of this invention to provide a catalytic process for reacting an organic monohydroxy compound (alcohol or phenol) with a 1,2 or 1,3 epoxide to produce a monomeric ether of a glycol, or a polyalkylene glycol in which process the catalyst is reusable and easily separated from the reaction mixture.

SUMMARY OF THE INVENTION

It has been found that insoluble polymers, having a carbon to carbon backbone cross-linked with carbon to carbon atoms and having tetraalkyl phosphonium alkoxide, cycloalkyloxide, aryloxide, or hydroxide group or a mixture of such groups attached to a pendant group of the polymer chain are good, heat stable catalysts for accelerating the reaction between a monohydroxy compound, preferably an alkanol or phenol and a 1,2 or 1,3 epoxide, preferably a 1,2 epoxide of 2–4 C atoms.

The reaction can be carried out at temperatures between about 50° C. and about 150° C.

The molar ratio of monohydroxy compound to epoxide can range from about 0.5 to 1 to about 0.5 to 20. When the molar ratio is about 1 to 1 the predominant product is a monoether of a monoglycol, but at high conversions appreciable amounts of product having the generic formula A(OA')$_2$OH are formed and small amounts of products where the integer is at least three are present in the mixture. As the molar ratio of epoxide is increased, the amount of products in which the integer is 2 or greater also increases.

Any compound with an OH and no other group which is reactive, as indicated below, and which is either liquid at reaction temperature or is soluble in an inert solvent, i.e., which is not reactive with the hydroxy compound, catalyst, epoxide or final product can be employed. For the purpose of this invention aromatic compounds with an OH group on the ring or an aliphatic or cycloalkyl alcohols are included. Preferably, the hydroxyl containing compound contains from 1 to about 10 carbon atoms and is free of nonaromatic unsaturation. The most preferred are unsubstituted monohydroxy compounds which have from 1 to about 6 C atoms.

The epoxides which can be reacted include those having from 2 to about 8 c atoms. Vicinal epoxides and those having a trimethylene

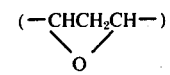

group in their structure are operative. The epoxide can be terminal or a nonterminal group. Representative epoxides include ethylene oxide, propylene oxide, 1,3-trimethylene oxide, 1,2; 2,3 or 1,3 butylene oxides, styrene oxide, cyclohexene oxide or cyclopentene oxide.

The molar ratio of catalyst to the organic hydroxy compound can range from about 0.001 to about 0.5, but amounts greater than about 0.02 are not needed for satisfactory results.

The catalysts can be prepared by reacting a cross-linked polymer having -(CH$_2$)$_n$ or m Y groups (where Y is a halogen, preferably Cl, Br or I) attached to a pendant linkage of the main polymer chain with a trialkylphosphine and then converting the latter to an alkoxide, aryloxide, or hydroxide group.

Detailed methods for the preparation of catalysts having $\phi$-(CH$_2$)$_n$P$^+$(R)$_3$X$^-$ and —CO$_2$(CH$_2$)$_m$P$^+$(R)$_3$X$^-$ groups are given in our copending patent application entitled "Insoluble Polyalkyl Phosphonium Salt Resins", now U.S. Pat. No. 3,919,126 granted Nov. 11, 1975, filed of even date herewith and are incorporated herein by reference.

In general, a copolymer containing a plurality of —(CH$_2$)$_n$ or m Y groups, as above defined, can be reacted with a trialkyl phosphine to form —(CH$_2$)$_n$ or m P$^+$(R)$_3$Y$^-$ groups. The latter groups are then converted to —(CH$_2$)$_n$ or m P$^+$(R)$_3$X$^-$ groups either directly by reaction with an alkali metal alkoxide in instances where Y is Cl or Br or indirectly by reacting the tetraalkyl phosphonium halide group with a carboxylic acid salt and then exchanging the acid group for an alkoxy group.

The examples which follow are intended to illustrate, but not limit, the invention,

PREPARATION OF THE CATALYST

The catalyst of this example was prepared from a cross-linked copolymer of a 2:1 molar ratio of styrene and p-bromo styrene and 2% by weight, based on the above monomers, of divinyl monomers. The latter in this instance was divinyl benzene. The Br of the polymer was replaced with Li and then the Li was converted to —(CH$_2$)$_3$OH by reaction with trimethylene oxide. The OH of the —(CH$_2$)$_3$OH was converted to the iodide with I$_2$ in the presence of triphenyl phosphine. The cross-linked polymer having a plurality of —(CH$_2$)$_3$I groups was then reacted with triethyl phosphine to form the corresponding triethyl n-propyl phosphonium iodide. The iodide was converted to the acetate with sodium acetate and the acetate was converted to —OC$_2$H$_5$/OH$^-$ by reaction with an 80-20 ethanol-water mixture (by volume) containing 3.7 g. Na in 200 ml. of the ethanol-water mixture. This catalyst had a plurality of

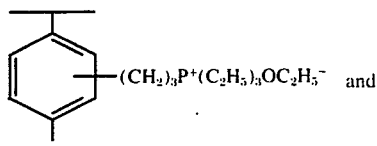

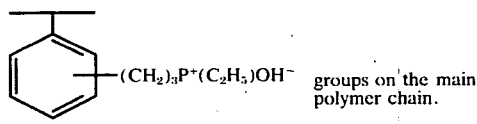 groups on the main polymer chain.

Tetraalkyl phosphonium bromides or chlorides can be reacted directly with the alcohol-water-alkali metal reaction solution to convert the tetraalkyl phosphonium bromide or choride directly to the alkoxide and/or hydroxide.

Catalysts based on a cross-linked methacrylate resin having a plurality of

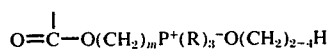

pendant groups were prepared by copolymerizing a 1:1 molar mixture of 3-bromopropyl methacrylate and styrene and 1.7 weight percent of divinyl benzene. A portion of the cross-linked insoluble, resin was reacted with triethylphosphine and another portion was reacted with tributylphosphine. One polymer, containing $-(CH_2)_3P^+(C_2H_5)_3Br^-$ groups, was converted to the acetate and then treated with sodium ethoxide/sodium hydroxide in ethanol/$H_2O$ to provide a plurality of $-(CH_2)_3P^+(CH_2H_5)_3{}^-{}_{OC2H5}/OH$ groups on the pendant ester group of the polymer chain and the other contained a plurality of $-(CH_2)_5P^+(C_4H_9)_3{}^-OC_2H_5$ or $(CH_2)_3P^+(C_4H_9)_3OH^-$ groups.

Catalysts based on cross-linked copolymers of a vinyl benzene monomer conforming to the formula

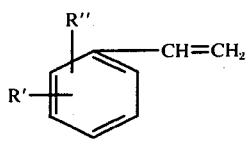

and a maleic ester conforming to the formula

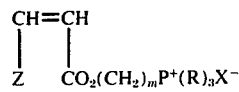

are made in a manner similar to that described for the acrylate ester, by merely substituting a diester of maleic acid containing 1 or 2 $(CH_2)_mY$ groups in the ester moiety for the acrylate ester. In the above formulae, R' can be H, a methyl, ethyl, propyl, isopropyl, butyl or isobutyl group or a combination of such groups, R'' is H or $CH_3$ and Z is a $CO_2(CH_2)_mP^+(R)_3X^-$ or a $CO_2$ alkyl group in which alkyl chain has from 1 to 10 C atoms, preferably 2 to 6 C atoms.

In the examples which follow mole ratios of reactants are used unless otherwise specifically indicated. The examples are intended to illustrate, but not to limit the invention.

EXAMPLE 1

In this and all subsequent examples, runs were made either in aerosol compatability tubes or in pressure tubes. The catalyst was weighed and placed in the tube and then preswollen with ethanol. The polymeric resin catalysts were weighed as solvent-swollen beads, in which the approximate amount of solvent was known. The organic monohydroxide compound and the epoxy compound were added in varying molar ratios. The reaction mixture was stirred for the indicated time at the indicated temperature. After reaction the mixture was cooled and the polymeric catalyst beads were separated from the liquid. In cases in which the polymeric beads were to be reused as catalysts for subsequent reactions, the beads were washed with ethanol prior to reuse.

The reaction mixtures were analyzed by gas-liquid chromatography using a QF1 column.

In this series, the reaction temperature was about 100° C. and the time was about 3.5 hours for each run. The catalyst had about 1.58 millimole of P per gram. The catalyst in runs 1 and 2 was made by reacting the corresponding phosphonium iodide with sodium phenate and sodium acetate, respectively and then converting to the alkoxide/hydroxide with sodium ethoxide/hydroxide. The catalyst for run 3 was made by reacting the corresponding phosphonium chloride with sodium ethoxide.

Tabulated below are the results of the runs.

Table 1

| Run No. | Catalyst | Molar Ratio of Reactants | | | Cycle | Percent Reaction |
|---|---|---|---|---|---|---|
| | | Catalyst | EtOH | PO* | | |
| 1 | ⟩—◯—$(CH_2)_3$—$P^+$—$(C_2H_5)_3OC_2H_5{}^-$ | 0.004 | 1.0 | 1.0 | 1<br>2<br>3 | 100<br>82<br>52 |
| 2 | ⟩—◯—$(CH_2)_3P^+(C_2H_5)_3OC_2H_5{}^-$ | 0.003 | 1.0 | 1.0 | 1<br>2<br>3<br>4<br>5 | 100<br>100<br>98<br>81<br>56 |
| 3 | ⟩—◯—$(CH_2)_3$—$P^+$—$(C_2H_5)_3OC_2H_5{}^-$ | 0.0025 | 1.0 | 1.0 | 1<br>2<br>3<br>4<br>5 | 99<br>99<br>99<br>90<br>65 |

Table 1-continued

| Run No. | Catalyst | Molar Ratio of Reactants | | | Cycle | Percent Reaction |
| --- | --- | --- | --- | --- | --- | --- |
| | | Catalyst | EtOH | PO* | | |
| 4 |  —(CH$_2$)$_3$P$^+$(n—C$_4$H$_9$)$_3$OC$_2$H$_5$$^-$ | 0.004 | 1.0 | 1.0 | 1<br>2<br>3 | 100<br>99<br>80 |

*PO = propylene oxide

These data show that the tetraalkyl phosphonium alkoxides are quite active as catalysts for the reaction of an epoxide with an alkanol and that appreciable catalytic activity can be retained after several cycles. The amount of diadduct was about 10% and triadduct about 2%.

EXAMPLE 2

The catalyst used in run 2 of example 1 was used for reacting propylene oxide at various molar ratios with the monohydroxy compounds specified. The temperature was 100°C. and the reaction time was 3.5 hours for each of the phenols and 7 hours for the tridecyl alcohol. Data for these runs are given below:

| Monohydroxy Compound (ROH) | Ratio (Molar) | | | Relative Glc Area | | | | | Product Color |
| --- | --- | --- | --- | --- | --- | --- | --- | --- | --- |
| | | | | Reactants | | Products | | | |
| | Cat. | ROH | PO | ROH | PO | Mono Adduct | Di Adduct | Tri Adduct | |
|  | 0.01 | 1 | 2 | 0 | 70 | 130 | 95 | | Faint Yellow |
|  | 0.021 | 1 | 4.2 | trace | 27 | 3.5 | 77 | 70 | Colorless |
| Tridecyl OH | 0.015 | 1 | 3.0 | trace | 40 | 87 | 80 | | Colorless |

1 G/C areas only were determined.
2 Each —C$_4$H$_9$ is a secondary butyl group.

The above data indicate that increasing the ratio of the epoxide results in increase of the number of epoxy derived groups in the end product.

EXAMPLE 3

The catalyst for this run was one having a plurality of

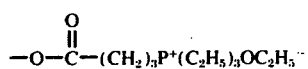

$$-O-\overset{O}{\underset{\|}{C}}-(CH_2)_3P^+(C_2H_5)_3OC_2H_5^-$$

or CO$_2$ (CH$_2$)$_3$P$^+$(C$_2$H$_5$)$_3$OH$^-$ groups attached to the polymer backbone. This catalyst was made from a cross-linked copolymer of styrene and a methacrylate ester by the procedure described above. It contained about 8% P. A reaction between C$_2$H$_5$ OH and propylene oxide was carried out by the procedure described in Example 1. The molar ratio of catalyst was 0.009 and that of ethanol and propylene oxide was 1 mole each. After 3.5 hours 100% of the alcohol and epoxide were reacted.

Similar results were obtained with a catalyst —CO$_2$(CH$_2$)$_3$P$^+$(n-C$_4$H$_9$)$_3$OC$_2$H$_5$$^-$ pendant groups.

The acrylate ester derived catalysts lose their activity much more rapidly than those derived from styrenes.

The catalysts derived from maleic acid esters behave in a manner which is similar to the acrylate esters.

We claim:

1. A method of preparing monethers of alkylene glycols comprising commingling a 1,2- or 1,3-epoxide having from 2 to about 8 C atoms with an unsubstituted monohydroxy compound having from 1 to 10 C atoms, at a temperature of from about 50° to about 150° C., in the presence of a catalytically active amount of a catalyst which is a polymer, insoluble in the reaction mixture, having a carbon to carbon backbone, cross-linked with carbon to carbon atoms, said polymer having a plurality of

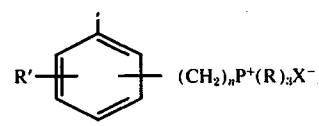

or CO$_2$ (CH$_2$)$_m$P$^+$(R)$_3$X$^-$ pendant groups wherein n is an integer from 1 to 3, m is an integer of from 1-6, R is an alkyl group of from 1 to about 6 C atoms, R' is H, CN or one or more alkyl groups having a total of up to 6 C atoms, and X is hydroxyl, an alkoxy group of 1-10 C atoms, a cycloalkoxy group of 5-10 C atoms or an aryloxy group of 6-10 C atoms.

2. The method of claim 1 in which the catalyst has a plurality of

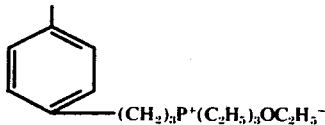

the epoxide is propylene oxide and the monohydroxy compound is ethanol.

3. The method of claim 2 in which the molar ratio of propylene oxide to ethanol is 1 to 1 and the molar ratio of catalyst to ethanol is 0.0025 to 0.004.

4. The method of claim 1 in which the catalyst has a plurality of

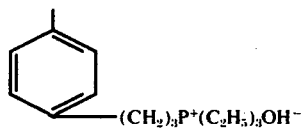

the epoxide is propylene oxide and the monohydroxy compound is ethanol.

5. The method of claim 1 in which the monohydroxy compound is phenol and the epoxide is propylene oxide.

6. The method of claim 1 in which the monohydroxy compound is 2,6-di-secondary butyl phenol and the epoxide is propylene oxide.

7. The method of claim 1 in which the monohydroxy compound is tridecyl alcohol and the epoxide is propylene oxide.

8. The method of claim 1 in which the catalyst has a plurality of $-CO_2(CH_2)_mP^+(R)_xX^-$ groups, the epoxide is propylene oxide and monohydroxy compound is ethanol.

9. The method of claim 8 in which the catalyst has a plurality of $-CO_2(CH_2)_3P^+(C_2H_5)_3OC_2H_5^-$ groups.

10. The method of claim 8 in which the catalyst has a plurality of $CO_2(CH_2)_3P^+(C_2H_5)_3OH^-$ groups.

11. The method of claim 8 in which the catalyst has a plurality of $CO_2(CH_2)_3P^+(n-C_4H_9)_3OC_2H_5^-$ groups.

12. The method of claim 8 in which the catalyst has a plurality of $(CH_2)_3P^+(n-C_4H_9)_3OH^-$ groups.

13. The method of claim 1 in which the catyst contains a plurality of

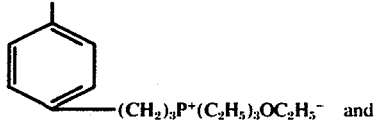

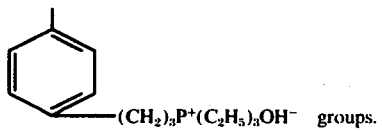

14. The method of claim 8 in which the catalyst contains a plurality of $CO_2(CH_2)_mP^+(CH_2)_{3\text{-}4}OC_2H_5^-$ and $CO_2(CH_2)_mP^+(CH_2)_{3\text{-}4}OH^-$ groups.

* * * * *

UNITED STATES PATENT AND TRADEMARK OFFICE
CERTIFICATE OF CORRECTION

PATENT NO. : 4,011,268

DATED : March 8, 1977

Page 1 of 2

INVENTOR(S) : Suzanne V. McKinley & Joseph W. Rakshys, Jr.

It is certified that error appears in the above-identified patent and that said Letters Patent are hereby corrected as shown below:

Col. 1, line 16, delete "catalyst" and insert -- catalysts --.

Col. 2, line 4, delete "c" and insert -- C --.

Col. 2, lines 23 and 37, delete " $-(CH_2)_n$ or m Y groups " and insert -- $-(CH_2)_{n \text{ or } m}$ Y groups --.

Col. 2, line 40, delete "$-(CH_2)_n$ or m $P^+(R)_3 X^-$" and insert -- $-(CH_2)_{n \text{ or } m} P^+(R)_3 X^-$ --.

*See pg. 2, re Col. 2, lines 38-39.

Col. 3, line 18, delete "choride" and insert -- chloride --.

Col. 3, line 35, delete " $-(CH_2)_3 P^+(CH_2H_5)_3{}^- oc2H_5/OH$ " and insert -- $-(CH_2)_3 P^+(C_2H_5)_3{}^- OC_2H_5/OH^-$ --

Col. 3, line 37, delete " $-(CH_2)_5 P^+(C_4H_9)_3{}^- OC_2H_5$ " and insert -- $-(CH_2)_3 P^+(C_4H_9)_3{}^- OC_2H_5$ --.

Col. 4, line 14, delete "Ch$_3$" and insert -- CH$_3$ --.

Col. 5, Example 3, line 55, delete " $-O-\overset{O}{\underset{\|}{C}}-(CH_2)_3 P^+(C_2H_5)_3 OC_2H_5{}^{\circ\cdot}$ "
and insert -- $-O-\overset{O}{\underset{\|}{C}}-(CH_2)_3 P^+(C_2H_5)_3 OC_2H_5{}^-$ --.

Col. 6, first line of Claim 1, delete "monethers" and insert -- monoethers --.

Col. 7, lines 10 and 26, in both instances before the words "the epoxide" insert -- groups, --.

UNITED STATES PATENT AND TRADEMARK OFFICE
CERTIFICATE OF CORRECTION

PATENT NO. : 4,011,268  
DATED : March 8, 1977  
Page 2 of 2

INVENTOR(S) : Suzanne V. McKinley & Joseph W. Rakshys, Jr.

It is certified that error appears in the above-identified patent and that said Letters Patent are hereby corrected as shown below:

Sheet 2

Col. 8, line 5, delete " $-CO_2(CH_2)_m P^+(R)_x X^-$ " and insert -- $-CO_2(CH_2)_m P^+(R)_3 X^-$ --.

Col. 8, in the first lines of Claims 10, 11, and 13, delete "catayst" and insert -- catalyst --.

*Col. 2, lines 38-39, delete " $-(CH_2)_n$ or m $P^+(R)_3 Y^-$ " and insert -- $-(CH_2)_{n \text{ or } m} P^+(R)_3 Y^-$ --.

Signed and Sealed this

Twenty-eighth Day of June 1977

[SEAL]

Attest:

RUTH C. MASON  
Attesting Officer

C. MARSHALL DANN  
Commissioner of Patents and Trademarks